(12) United States Patent
Powell et al.

(10) Patent No.: US 11,155,529 B2
(45) Date of Patent: Oct. 26, 2021

(54) METHODS FOR PRODUCING FERRIC MALTOL COMPOSITIONS FROM ELEMENTAL IRON

(71) Applicant: Shield TX (UK) Limited, Gateshead (GB)

(72) Inventors: Jonathan Joseph Powell, Cambridge (GB); Nuno Jorge Rodrigues Faria, Milton Ernest (GB)

(73) Assignee: SHIELD TX (UK) LIMITED, Tyne And Wear (GB)

( * ) Notice: Subject to any disclaimer, the term of this patent is extended or adjusted under 35 U.S.C. 154(b) by 0 days.

(21) Appl. No.: 16/089,788

(22) PCT Filed: Mar. 31, 2017

(86) PCT No.: PCT/EP2017/057702
§ 371 (c)(1),
(2) Date: Sep. 28, 2018

(87) PCT Pub. No.: WO2017/167969
PCT Pub. Date: Oct. 5, 2017

(65) Prior Publication Data
US 2020/0308130 A1   Oct. 1, 2020

(30) Foreign Application Priority Data
Mar. 31, 2016 (GB) ................................. 1605493

(51) Int. Cl.
| C07D 309/40 | (2006.01) |
| C01G 21/00 | (2006.01) |
| A61K 9/00 | (2006.01) |

(52) U.S. Cl.
CPC ......... *C07D 309/40* (2013.01); *C01G 21/003* (2013.01); *A61K 9/0053* (2013.01)

(58) Field of Classification Search
CPC ... C07D 309/40; C01G 21/003; A61K 9/0053

USPC ......................................................... 514/460
See application file for complete search history.

(56) References Cited

U.S. PATENT DOCUMENTS 4,830,716 A   5/1989   Ashmead

FOREIGN PATENT DOCUMENTS

| CN | 101857537 | 10/2010 |
| JP | S63-079859 | 4/1988 |
| JP | 2014-503579 | 2/2014 |
| RU | 2 304 575 | 8/2007 |
| WO | WO 03/097627 | 11/2003 |
| WO | WO 2011/006763 | 1/2011 |
| WO | WO 2012/101442 | 8/2012 |
| WO | WO 2015/101971 | 1/2015 |

OTHER PUBLICATIONS

Gasche et al. "Ferric maltol is effective in correcting iron deficiency anemia in patients with inflammatory bowel disease: results from a phase-3 clinical trial program." *Inflammatory Bowel Diseases* 21.3 (2014): 579-588.
Harvey, R. S. J., et al. "Ferric trimaltol corrects iron deficiency anaemia in patients intolerant of iron." *Alimentary pharmacology & therapeutics* 12.9 (1998): 845-848.
International Search Report and Written Opinion issued in International Application No. PCT/EP2017/057702, dated May 15, 2017.
Search Report issued in United Kingdom Application No. 1605493. 4, dated Jan. 23, 2017.
Machine Translation of CN 101857537, published Oct. 13, 2010.
Machine Translation of RU 2 304 575, published Aug. 20, 2007.
Office Communication issued in Japanese Application No. 2018-552009, dated Mar. 2, 2021.

*Primary Examiner* — Kristin A Vajda
(74) *Attorney, Agent, or Firm* — Parker Highlander PLLC

(57) ABSTRACT

Methods for producing ferric maltol compositions, such as ferric trimaltol, from elemental iron, and ferric maltol compositions produced by these methods and their uses are described.

16 Claims, 1 Drawing Sheet

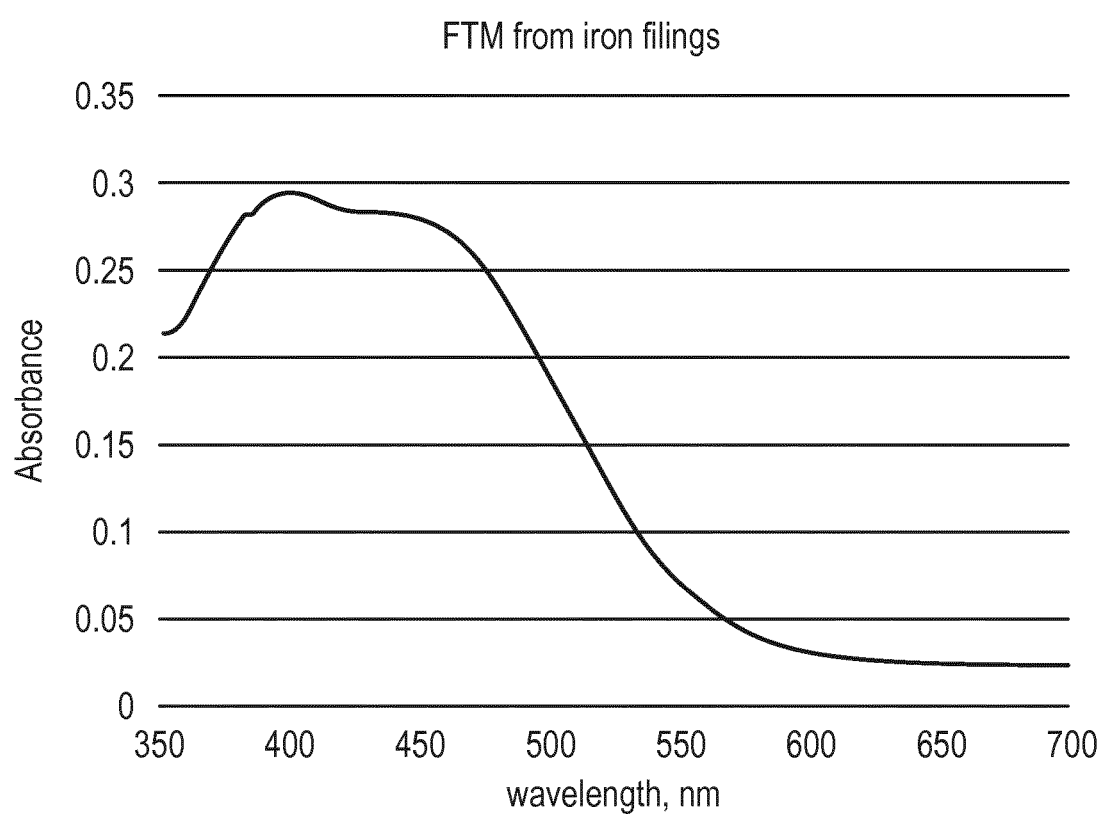

_METHODS FOR PRODUCING FERRIC MALTOL COMPOSITIONS FROM ELEMENTAL IRON_

This application is a national phase application under 35 U.S.C. § 371 of International Application No. PCT/EP2017/057702 filed Mar. 31, 2017, which claims priority to United Kingdom Application No. 1605493.4, filed Mar. 31, 2016. The entire text of each of the above referenced disclosures is specifically incorporated herein by reference.

FIELD OF THE INVENTION

The present invention relates to methods for producing ferric maltol compositions, such as ferric trimaltol, from elemental iron, and to ferric maltol compositions produced by these methods and their uses.

BACKGROUND OF THE INVENTION

The sugar derivative maltol is a hydroxypyrone (IUPAC name: 3-hydroxy-2-methyl-4H-pyran-4-one) and it strongly chelates iron and the resulting complex (ferric trimaltol) is well absorbed, unlike many other ferric iron therapies. Ferric trimaltol appears well tolerated even in populations highly susceptible to gastrointestinal side-effects, such as IBD patients (Harvey et al., 1998), and as such it provides a valuable alternative to patients who are intolerant of oral ferrous iron products, notably in place of intravenous iron. Clinical trials using ferric trimaltol have been carried out, see for example, Gasche et al., 2015.

However, despite the evidence of bioavailability and tolerability for ferric trimaltol, its clinical development has been limited by the absence of adequate synthetic routes. In particular, most manufacturing processes require the use of organic solvents, which increase manufacturing costs, for example to deal with post-synthesis solvent removal, and require additional safety measures, for example to deal with flammability. Critically, solvent-based syntheses are not robust and often generate ferric hydroxide, described in the prior art to be an unwanted impurity of the synthesis.

WO 03/097627 (Vitra Pharmaceuticals Limited) describes the synthesis of ferric trimaltol from iron salts of carboxylic acids in aqueous solution at a pH greater than 7. In a first synthesis, ferric citrate is added to a solution of sodium hydroxide at room temperature and maltol is added to a second solution of sodium hydroxide at pH 11.6. The ferric citrate solution is added to the maltol solution, leading to the production of a deep red precipitate. This composition is then evaporated until dryness and the material is powdered and dried. Alternative syntheses are described using ferrous fumarate or ferrous gluconate as the iron carboxylate salt starting material, and by dissolving maltol in sodium carbonate solution in place of sodium hydroxide. However, despite the fact that this process is fully aqueous, several of the iron carboxylate salts employed are expensive, especially as they need to be pharmaceutical grade if the ferric trimaltol is to be suitable for human administration. More importantly, this process introduces high levels of carboxylates (equimolar to iron or greater) to the synthesis that are not easily removed by filtration or centrifugation of the ferric trimaltol cake. Instead these water soluble contaminants must be washed off (e.g. water washed), but this would result in considerable losses of the product due to the amphipathic nature of ferric trimaltol.

WO 2012/101442 (Iron Therapeutic Holdings AG) describes the synthesis of ferric trimaltol by reacting maltol and a non-carboxylate iron salt in an aqueous solution at alkaline pH. However, despite the lower cost of non-carboxylate iron salts, pharmaceutically appropriate grades are still required if the ferric trimaltol is to be suitable for human administration and hence are comparatively expensive starting materials. Importantly, the use of non-carboxylate iron salts (e.g. ferric chloride) results in the addition of considerable levels of the respective counter-anion (e.g. three moles of chloride per every mole of iron) of which a significant part is retained in the filtration (or centrifugation) cake and thus must be washed off. As such, WO 2012/101442 does not address the problem of product losses in WO 03/097627. Furthermore, the addition of a non-carboxylate iron salt (e.g. ferric chloride) to a very alkaline solution, as described in WO 2012/101442, promotes the formation of stable iron oxides, which is an unwanted contaminant in ferric trimaltol. As a consequence, further costly and time-consuming processing of the material would be required for manufacturing.

Overall, the cost of the current aqueous syntheses is driven by regulatory demands for low levels of toxic heavy metals and residual reagents in the final pharmaceutical formulation, which force the use of highly purified, and thus expensive, iron salts as well as thorough washing of the final product (resulting in significant losses of product). This will impact on the final price of ferric trimaltol and potentially limits patient access to this therapy. As such, there is a need for a process that can use lower iron grades and limited wash cycles whilst producing ferric trimaltol of adequate purity.

Accordingly, it remain a problem in the art to provide processes for the synthesis of ferric trimaltol at economic cost and which overcome some or all of the drawbacks set out above that are associated with prior art. Solving these issues, through better synthesis of the material would allow good patient access to ferric trimaltol.

SUMMARY OF THE INVENTION

Broadly, the present invention relates to methods for producing ferric maltol compositions, such as ferric trimaltol, in which maltol is reacted with elemental iron. Surprisingly, elemental iron (zero valence), which is not an obvious source of iron in complexation syntheses aiming to produce ferric iron complexes, was found to be an appropriate reagent in the synthesis of ferric trimaltol (Fe at +3 valence) provided that an adequate source of oxygen is available. Usefully, unreacted elemental iron may be removed magnetically thus providing a straightforward and cheap clean-up strategy. Additionally, the methods of the present invention enables the use of a cheap source of iron (i.e. elemental iron) unlike previous processes. Importantly, unlike previous syntheses that use ferric salts, the process described herein does not produce high levels of unwanted ionic species (e.g. citrate or chloride) and thus clean-up processes may be simpler and cheaper.

The process described herein provides the further advantage of enabling a one-step synthesis from elemental iron in a single vessel. This is possible because, unlike previously disclosed syntheses, the present process does not result in the release of unwanted counter anions (e.g. chloride, carboxylates). The reactions may also have the advantage of being carried out using fully aqueous conditions.

Accordingly, in a first aspect, the present invention provides a method for producing ferric maltol comprising reacting elemental iron with maltol, typically in the presence of oxygen, and recovering the ferric maltol that forms. In a preferred embodiment, the present invention provides a method for producing ferric trimaltol composition comprising reacting elemental iron with maltol and recovering the ferric trimaltol that forms. Ferric maltol will form from the mixing of elemental iron with maltol under aqueous conditions, but the reaction rate is greatly enhanced when supplemental oxygen is made available. The reaction is typically carried out under alkaline conditions.

The present inventors observed that the process of oxidation of elemental iron to ferric iron, which is essential for the production of ferric maltol compositions, can be accelerated by delivering compressed oxygen to the reaction. Conveniently, oxygen also can be delivered to the reaction using compressed air for example or stirring and mixing techniques or generated by other means known in the art.

As set out above therefore, a still further advantage is that the methods for producing ferric maltol compositions according to the present invention may enable single vessel synthesis, for example using a single manufacturing vessel, such as a filtration unit with overhead stirring.

Conveniently in the methods of the present invention, an oxidising agent, such as hydrogen peroxide, can be added to accelerate the conversion from elemental to ferric iron, thus reducing the duration of the synthetic process.

Additionally or alternatively other complexing agents (e.g. carboxylates or amino acids) may be added to the synthesis to accelerate dissolution and act as donors of iron for high affinity maltol chelation. However, this may be a less desirable embodiment since the additional reactants would require more extensive clean up processes.

Generally, the ferric maltol composition is produced from an elemental iron suspension at 0.2M, or 0.5 M, or 1 M Fe or greater. Conveniently, the elemental iron is added to a maltol solution at a maltol concentration of 0.6M or greater, 1.5M or greater, or 3M or greater. By way of illustration, the elemental iron is added to a maltol solution to achieve a maltol to iron ratio in solution equal to or greater than 3.0 and lower than 4.0, and more preferably greater than 3.1 and lower than 3.75.

By way of illustration, at the start of the synthesis, elemental iron is added to a maltol solution which is at a pH greater than 8.5, preferably greater than 9.0, more preferably greater than 9.5, even more preferably greater than 10, most preferably greater than 10.6.

In a further aspect, the present invention provides a method for producing an iron supplement comprising ferric maltol, the process comprising having produced a ferric maltol composition according to a method as described herein, the further step of formulating the ferric maltol for administration to a subject.

Embodiments of the present invention will now be described by way of example and not limitation with reference to the accompanying FIGURES. However, various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

BRIEF DESCRIPTION OF THE FIGURES

FIG. 1. UV-vis spectra of FTM produced from elemental iron (as per example 1). The two band profile is characteristic of FTM recovered from an alkaline environment. UV vis conditions: Perkin Elmer Lambda 25; 700-350 nm; 480 nm/min; 0.5 nm interval.

DETAILED DESCRIPTION

Ferric Maltols

Ferric maltols are a class of compounds that include ferric trimaltol, a chemical complex formed between ferric iron ($Fe^{3+}$) and the hydroxypyrone, maltol (IUPAC name: 3-Hydroxy-2-methyl-4H-pyran-4-one), in a molar ratio of ferric iron to maltol of 3:1. Maltol strongly chelates the ferric iron and the resulting complex (ferric trimaltol) is well absorbed, in contrast to some other ferric iron supplements, fortificants and therapies. Maltol binds metal cations mainly in the form of a dioxobidentate ligand in a similar manner proposed for other 4(1H)-pyranones:

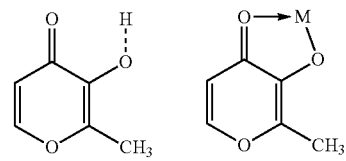

Structure of maltol (3-hydroxy-2-methyl-4(H)-pyran-4-one) and dioxo-chelation to metal cations (M) such as iron. For ferric trimaltol three maltol groups surround one iron.

However, particularly in aqueous environments, it is well known that concentration-dependent and pH-dependent equilibrium species of ferric maltol can form that include oligomeric species such as dimers and/or ferric iron species complexed with one or two maltol molecules. Ferric trimaltol in solid or powder form may also exist as oligomers including dimers and not every iron is necessarily co-ordinated to three maltol molecules, but the term ferric tri-maltol is conventionally used in the art. Accordingly, in the present application, references to "ferric maltol" are intended to include ferric iron species complexed with one, two or three maltol species, as well as oligomeric species such dimers and other species that may exist in equilibrium with them, and to mixtures of any of these species, even though the behaviour of the complex is believed to be dominated by its trimaltol form at supplemental levels.

The structure of ferric trimaltol is shown in WO 2015/101971 (Iron Therapeutics Holdings AG). Ferric trimaltol is also known as "ST10" and is generally administered as a 30 mg dose, where 30 mg refers to the amount iron in the dose. The amount of ST10 equivalent to 30 mg of elemental iron ($Fe^{3+}$) is 231.5 mg. Ferric trimaltol has undergone clinical trials for the treatment or prevention of anaemia in particular in patients with inflammatory bowel disease (IBD) or in patients with intolerance of iron.

Elemental Iron

Elemental iron (zero valence iron) despite being poorly absorbed is commonly used in food fortification, mostly due to its very low cost for a form of iron with acceptable purity for oral administration to a subject. Elemental iron nomenclature is typically determined by its production processes, comprising, but not limited to, atomised, reduced, electrolytic and carbonyl iron. Food grade batches typically consist of materials with small particle size, generally achieved through micronisation. Such small particle size materials offer a high surface to volume ratio and as such are particularly suitable for conversion to ferric trimaltol, using the synthetic process described herein.

It will be obvious to those in the art that despite ferric trimaltol being at a maltol-to-iron ratio of 3.0, greater ratios may be used in the reaction vessel. In particular, elemental iron may be added to a maltol solution to achieve a maltol-to-iron ratio in solution equal to or greater than 3 and lower than 4.0 and more preferably greater than 3.1 and lower than 3.75.

The oxidation of elemental iron and the complexation of ferric ions by maltol are favoured at alkaline pHs and consequently the inventors observed that the process described herein is best conducted at alkaline pHs. In particular, elemental iron may be added to a maltol solution which is at a pH greater than 8.5, preferably greater than 9.0, more preferably greater than 9.5, even more preferably greater than 10, most preferably greater than 10.6. The pH can be adjusted with by addition of a base, preferably sodium hydroxide or sodium carbonate.

Ferric Maltol Compositions and their Uses

The ferric maltol compositions produced according to the methods of the present invention may be formulated for administration to an individual and contain in addition to ferric trimaltol, a pharmaceutically acceptable excipient, carrier, buffer, stabiliser or other materials well known to those skilled in the art. Such materials should be non-toxic and should not interfere with the efficacy of the solid phase materials for the application in question.

As described herein, ferric maltols, such as ferric trimaltol, have particular uses in the treatment of iron deficiency. By way of example, the ferric trimaltol compositions may be used to deliver iron to an individual for use in the prophylaxis or treatment of iron deficiency or iron deficiency anaemia which may be suspected, or diagnosed through standard haematological and clinical chemistry techniques. Iron deficiency and iron deficiency anaemia may occur in isolation, for example due to inadequate nutrition or due to excessive iron losses, or they may be associated with stresses such as pregnancy or lactation, or they may be associated with diseases such as inflammatory disorders, cancers and renal insufficiency. In addition, there is evidence that the reduced erythropoiesis associated with anaemia of chronic disease may be improved or corrected by the effective delivery of systemic iron and that co-delivery of iron with erythropoietin or its analogues may be especially effective in overcoming reduced erythropoietic activity. Thus, by way of further example, the ferric trimaltol compositions disclosed herein may be used to deliver iron to an individual for use in the treatment of sub-optimal erythropoietic activity such as in anaemia of chronic disease. Anaemia of chronic disease may be associated with conditions such as renal insufficiency, cancer and inflammatory disorders. As noted above, iron deficiency may also commonly occur in these disorders so it follows that treatment through iron supplementation may address iron deficiency alone and/or anaemia of chronic disease. It will be recognised by those skilled in the art that the above examples of the medical uses of iron supplements are by no means limiting.

In addition, ferric trimaltol is currently used for the treatment or prevention of anaemia in particular in patients with inflammatory bowel disease (IBD) or in patients with intolerance to other forms of oral iron.

The precise nature of the carrier or other component may be related to the manner or route of administration of the composition. These compositions may be delivered by a range of delivery routes including, but not limited to: gastrointestinal delivery, including orally and per rectum or by implantation at specific sites, including prosthetics that may be used for this purpose or mainly for another purpose but have this benefit.

Pharmaceutical compositions made according to the present invention are generally for oral administration and may be in a tablet, capsule, powder, gel or liquid form. A tablet may include a solid carrier such as gelatin or other excipients. Capsules may have specialised properties such as an enteric coating. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

The ferric trimaltol compositions used in accordance with the present invention that are to be given to an individual are preferably administered in a "prophylactically effective amount" or a "therapeutically effective amount" (as the case may be, although prophylaxis may be considered therapy), this being sufficient to show benefit to the individual (e.g. bioavailability). The actual amount administered, and rate and time-course of administration, will depend on the nature and severity of what is being treated. Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, Lippincott, Williams & Wilkins. A composition may be administered alone or in combination with other treatments, either simultaneously or sequentially, dependent upon the condition to be treated.

In general, ferric trimaltol may be used as a form of oral iron supplementation for nutritional or medical benefit. In this area, there are three main examples:

(i) Therapeutic (prescription) supplements, which are generally administered by the oral or i.v. routes for the treatment of indications including iron deficiency anaemia, iron deficiency and anaemia of chronic disease. The therapeutic administration of materials of the present invention may be in conjunction with other therapies and especially with the concomitant use of erythropoietin.

(ii) Nutritional (self prescribed/purchased supplements) which are usually for oral delivery.

(iii) Fortificants. These may be traditional forms—in terms of being added to food prior to purchase—or more recent fortificant forms such as 'Sprinkles' which are added (rather like salt or pepper) to food at the time of ingestion.

In all formats, but most especially for fortificants, subsequent formulation, such as addition of a protective coating (e.g. lipid), may be necessary to make the material compatible with its intended usage.

It will be recognised by those skilled in the art that the above examples of the medical uses of iron supplements are by no means limiting.

EXAMPLES

Example 1: FTM from Iron Filings 7 g of NaOH pellets were added to 50 mL UHP water and stirred until dissolved. Next, 24.5 g maltol were added and stirred until dissolved. Then, 3.07 g iron fillings were added and the resulting suspension was stirred whilst bubbling with oxygen. A considerable amount of dark red precipitate (i.e. FTM) was observable 48 hours later but the synthesis was allowed to continue for a further 3 days. Undissolved iron filings were then removed with a magnetic bar and FTM recovered by centrifugation (4500 rpm×10 min). The FTM material was then dried at 50±5° C. and its structure confirmed by analysis.

REFERENCES

All publications, patent and patent applications cited herein or filed with this application, including references filed as part of an Information Disclosure Statement are incorporated by reference in their entirety.

Gasche et al., Ferric maltol is effective in correcting iron deficiency anaemia in patients with inflammatory bowel disease: results from a phase-3 clinical trial program. *Inflamm Bowel Dis.,* 21(3):579-88, 2015.

Harvey et al., Ferric trimaltol corrects iron deficiency anaemia in patients intolerant of iron. *Aliment Pharmacol Ther.,* 12(9):845-8, 1998.

The invention claimed is:

1. A method for producing a ferric maltol composition comprising reacting elemental iron with maltol and recovering the ferric maltol that forms.

2. The method according to claim 1, wherein the ferric maltol is ferric trimaltol.

3. The method according to claim 1, wherein reacting elemental iron is carried out in the presence of oxygen and/or an oxidising agent.

4. The method according to claim 3, wherein the oxygen provided to the reaction using compressed air, oxygen or oxygen-enriched material.

5. The method according to claim 3, wherein oxygen is provided to the reaction using air achieved through mixing and thus aeration of the solution with atmospheric oxygen or by introduction of air by injection or pumping.

6. The method according to claim 1, further comprising adding a complexing agent to accelerate the conversion of elemental iron to ferric maltol.

7. The method according to claim 1, further comprising removing unreacted elemental iron with a magnet.

8. The method according to claim 1, wherein the method is carried out in fully aqueous conditions.

9. The method according to claim 1, wherein the ferric maltol is produced in a single vessel.

10. The method according to claim 1, further comprising separating.

11. The method according to claim 1, further comprising purifying and/or formulating the ferric maltol composition.

12. The method according to claim 1, further comprising mixing the ferric maltol composition with one or more excipients.

13. The method according to claim 1, further comprising formulating the ferric maltol composition for oral administration to a subject.

14. The method according to claim 10, further comprising drying the ferric maltol composition.

15. The method according to claim 1, wherein the molar ratio in solution of maltol to elemental iron is greater than 3.0 and less than 4.0.

16. The method according to claim 1, wherein maltol is provided in the form of a solution at a pH of greater than 8.5.

* * * * *